United States Patent [19]

Huebner

[11] Patent Number: 5,454,811
[45] Date of Patent: Oct. 3, 1995

[54] CAM LOCK ORTHOPEDIC FIXATION SCREW AND METHOD

[75] Inventor: Randall J. Huebner, Aloha, Oreg.

[73] Assignee: Smith & Nephew Dyonics, Inc., Andover, Mass.

[21] Appl. No.: 149,062

[22] Filed: Nov. 8, 1993

[51] Int. Cl.⁶ .................................................. A61B 17/68
[52] U.S. Cl. .................... 606/60; 606/72; 606/73
[58] Field of Search ................... 606/73, 76, 77, 606/72, 60; 411/411, 417, 418, 426; 623/13

[56] References Cited

U.S. PATENT DOCUMENTS

| | | | |
|---|---|---|---|
| 848,914 | 4/1907 | Matheson | 411/417 |
| 2,382,109 | 8/1945 | Miller | 85/41 |
| 3,741,205 | 6/1973 | Markolf et al. | |
| 4,041,939 | 8/1977 | Hall | |
| 4,927,421 | 5/1990 | Goble et al. | |
| 4,950,270 | 8/1990 | Bowman et al. | |
| 5,109,080 | 5/1991 | Hemer | 606/73 |
| 5,234,430 | 8/1993 | Huebner | 606/60 |
| 5,261,914 | 11/1993 | Warren | 606/73 |

FOREIGN PATENT DOCUMENTS

| | | |
|---|---|---|
| 0151263 | 8/1985 | European Pat. Off. |
| 0180532A1 | 5/1986 | European Pat. Off. |
| 0441065A2 | 8/1991 | European Pat. Off. |
| 0556571A1 | 8/1993 | European Pat. Off. |
| 3529009 | 2/1987 | Germany |
| 365613 | 12/1938 | Italy |
| 643131 | 5/1984 | Switzerland |
| 1667850 | 5/1989 | U.S.S.R. |
| 85/04568 | 10/1985 | WIPO ........................... 606/73 |
| WO-A-8806023 | 8/1988 | WIPO |
| 92/03980 | 3/1992 | WIPO ........................... 606/73 |

*Primary Examiner*—Tamara L. Graysay
*Attorney, Agent, or Firm*—Pravel, Hewitt, Kimball & Krieger

[57] ABSTRACT

A cam-locking orthopedic fixation device for anchoring a bone graft in a bore formed in a bone mass. The device has a head, a nose remote from the head, and a body, extending between the head and the nose, with a series of threaded crests only partially circumferentially surrounding the body. At least one side of the body is smooth and free of thread crests. The device is inserted into the space between a bone graft and a wall of the bore so that the side free of threads slides against bone. Upon complete insertion, a driving tool is coupled to the inserted head of the device. The device is then rotated so that threads cut into bone of both the graft and the bore thereby providing an interference fit between the walls of the bore and the bone graft that resists withdrawal of the bone graft from the bore.

8 Claims, 4 Drawing Sheets

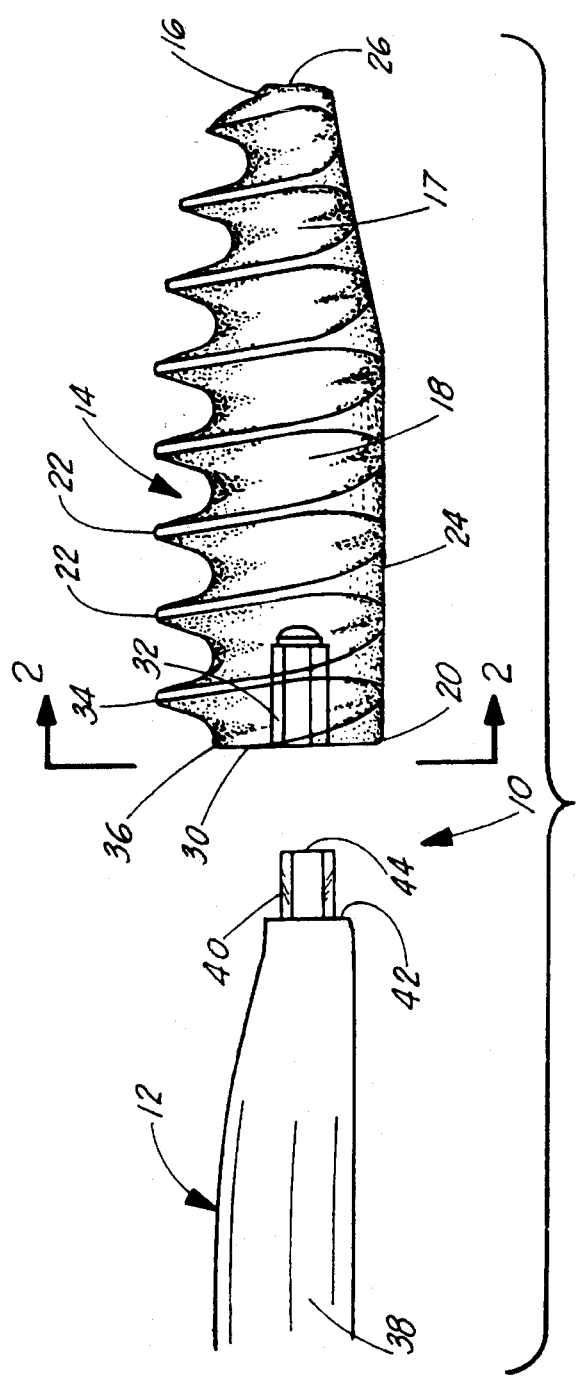
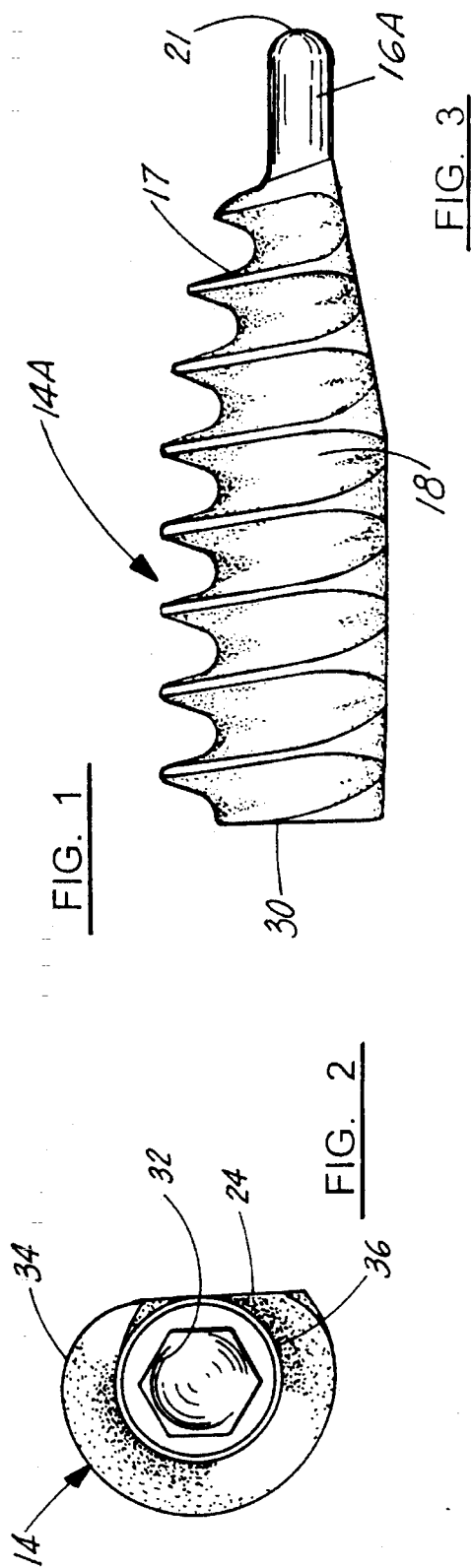
FIG. 1
FIG. 2
FIG. 3

CAM LOCK ORTHOPEDIC FIXATION SCREW AND METHOD

BACKGROUND OF THE INVENTION

1. Field of the Invention

The present invention relates to orthopedic fixation screws and methods and more particularly to such screws and methods in which a bone graft is anchored in a bore formed in a bone mass.

2. Description of the Related Art

The anterior cruciate ligament (ACL) is 25 mm–40 mm in length and is frequently injured in contact and other activities. Such injuries can cause instability in the knee to the extent that ACL reconstruction may be required.

The replacement of the ACL with the central third of the patellar tendon using a bone-tendon-bone graft is a known method for restoring knee stability. In this procedure, the central third of the patellar tendon and portions of bone at either end thereof are taken as a graft. A tunnel is bored in the distal femur and proximal tibia, i.e., where they join at the knee. The bone-tendon-bone graft is disposed with one bone segment in one of the tunnels and the other bone segment in the other tunnel. With the graft so disposed, each of the bone segments are anchored by screwing an interference screw into the tunnel between a tunnel wall and the bone segment thereby anchoring the segment in the tunnel.

Such procedure is illustrated and described in U.S. Pat. No. 4,927,421 to Goble et al. for process of endosteal fixation of a ligament. The Goble et al. method suffers from several disadvantages. First, the interference screw is cannulated, i.e., it has an axial bore for riding a guide wire into the bore. The wire must be inserted into the bore adjacent the bone graft before the screw can be installed. The guide wire prevents divergence of the screw as it is screwed into the space between the graft and the tunnel wall. A special driver, also having an axial bore for receiving the guide wire, must be provided to install the screw. Threading the wire through the bore is an additional surgical step, in itself undesirable, which has the potential for creating metal debris. In addition, the guide wires can bend or kink. The screw of the Goble et al. application provides an extremely steep taper at the leading end thereof which rapidly compresses the graft as the screw is installed.

SUMMARY OF THE INVENTION

The present invention comprises a cam-locking orthopedic fixation screw for anchoring a bone graft in a bore formed in a bone mass. The screw includes a head, a nose remote from the head, and a body having continuously tapered threads tapering from the head of the screw to the nose of the screw wherein one side of the screw, along the longitudinal axis is flat and unthreaded.

In accordance with the present invention, a method for securing a bone graft in an enosteal tunnel is presented. The method includes drilling an endosteal bore of a size sufficient to form a space between the bone graft and a wall of the bore when the graft is inserted in the bore, inserting the graft in the one end of the bore, inserting the bone screw into the space without rotating the screw and without cutting the bone, the bone screw having an asymmetrical cross section, and thereafter rotating the screw until its threads engage the bone graft and the bore wall thereby locking the screw in place and fixing the graft in the bore.

The present invention obviates the need for using a cannulated interference screw and further provides improved gradual compression of the graft as the fixation screw is installed.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 1 is an enlarged view of a cam-lock orthopedic fixation screw and a portion of a driver therefor constructed in accordance with the present invention.

FIG. 2 is a view along line 2—2 in FIG. 1.

FIG. 3 is an enlarged view, partly in cross-section, of an alternative embodiment of the cam-lock orthopedic fixation screw of FIG. 1.

DETAILED DESCRIPTION OF THE PREFERRED EMBODIMENT

Figure 4:
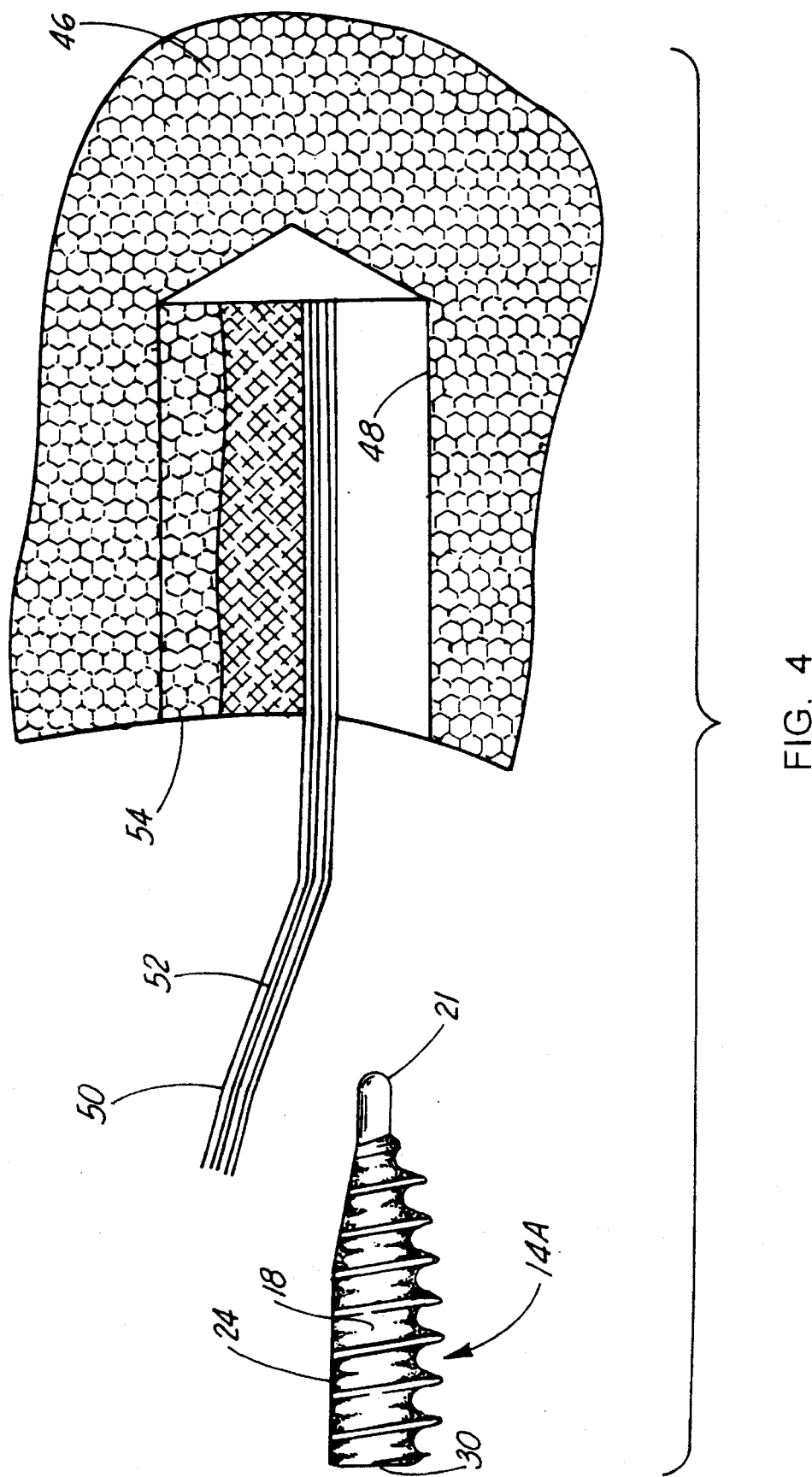
FIG. 4 is a view, partly in cross-section, of the screw of FIG. 3 prior to placement into the bone.

Turning first to FIG. 1, indicated generally at 10 is an orthopedic fixation device for anchoring a bone graft in a bore formed in a bone mass. Device 10 includes a driver 12 and screw 14. The screw includes a nose 16, a threaded body 18 and a head 20. The nose is remote from the head and threaded body 18 has continuously tapered threads 22 which taper from approximately midway between head 20 and nose 16. A tapered portion 17 extends for approximately three complete threads from the nose 16 to threaded body 18. One side 24 of the screw is asymmetrical and preferably flat and unthreaded. The present embodiment of screw 14 has a uniform pitch of ten threads per inch along the threaded portion thereof and has a nose 16 that has a flat leading face 26.

The head 20 of screw 14 includes an axial hexagonal socket 32. The socket walls are parallel to the axis of screw 14 and are sized to receive a conventional hexagonal driver. The height of the thread crest becomes progressively less between about thread crest 34 and the head 20 of the screw. A substantially 30° chamfer 36 is formed at the juncture between rear surface 30 and the root of threaded body portion 18. The progressive reduction of thread crest height thus forms a spiral between crest 34 and chamfer 36 as viewed in FIG. 2. Preferably, screw 14 is either constructed of a biocompatible material, or has a surface coating of biocompatible material, which is suitable for longterm emplacement in association with cancellous bone and soft tissues.

Driver 12 includes a shaft 38 having a driving end 40 formed on one end and a handle (not shown), similar to the handle of a screw driver, formed on the other end thereof. Driving end 40 comprises a hexagonal driver having walls which taper inwardly between the juncture 42 of driving end 40 with shaft 38 and the outer end 44 of driving end 40. As can be seen in FIG. 1, the distance between juncture 42 and end 44 is slightly less than the depth of socket 32. The relative sizes of driving end 40 and socket 32 are such that the hexagonal walls of driving end 40 engage the interior walls of socket 32 as the screw socket is fitted over driving end 40. Such engagement occurs just before rear surface 30 reaches juncture 42. Given that the interior walls of socket 32 are substantially parallel to the longitudinal axis of driver 12 while the walls of driving end 40 taper as described above, the screw can be fitted onto the end of driver 12 by pushing the screw until driving end 40 and socket 32 are tightly engaged.

FIG. 3 illustrates an alternative embodiment of the present invention. Indicated generally at 14A is a cam lock orthopedic fixation screw similar to the device illustrated in FIG. 1. The main difference is that screw 14A comprises an elongate nose 16A. Nose 16A includes a hemispherical leading face 21. The nose 16 is preferably at least twice the length of the diameter of the nose. A tapered portion 17 extends for approximately three complete threads from nose 16A to threaded body 18.

Turning now to FIG. 4, a bone mass 46 has a bore 48 formed therein. In the case of ACL reconstructive surgery, the bore is formed in either the distal femur or proximal tibia, or both when screw 14A is used to anchor both ends of a bone-tendon-bone graft. Bore 48 is also referred to herein as an endosteal tunnel. One end of the bone-tendon-bone graft is shown received in the bore 48. Graft 50 includes a tendon 52 and a bone portion 54 connected to the tendon. The other end of the tendon 52 (not shown) similarly includes a bone portion connected thereto.

Figure 5:
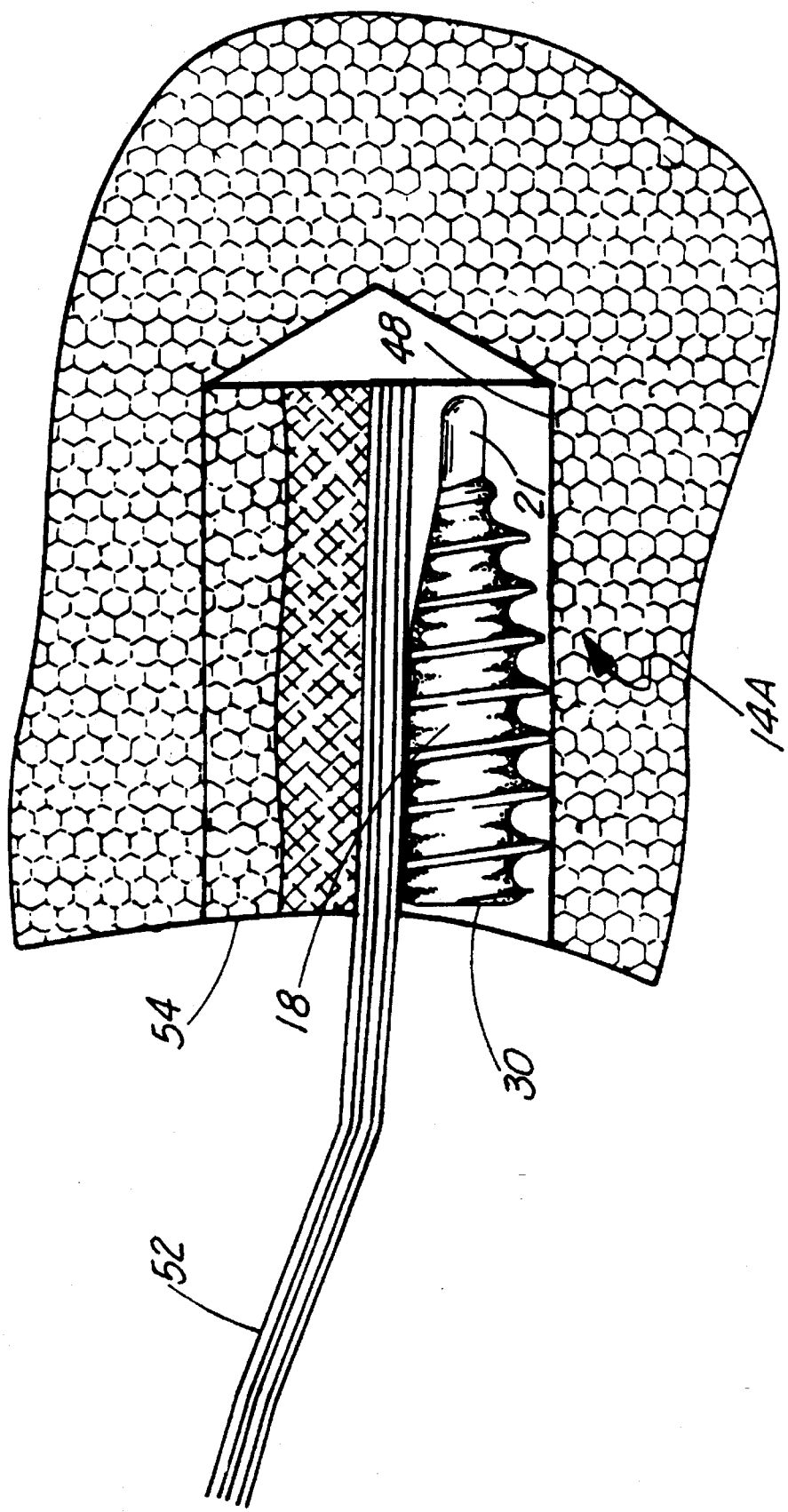
FIG. 5 is a view, similar to FIG. 4, after the screw has been inserted into the bone.

In use, an orthopedic surgeon bores hole 48 in bone mass 46 which, for purposes of the present explanation, is assumed to be the distal femur. This is accomplished using a conventional orthopedic drill and may be done endoscopically as may be the remainder of the following-described procedure. After bore 48 is drilled as shown in FIG. 4, one end of the graft 50 is positioned in the bore as illustrated. Screw 14A is fitted onto driver 12 as described above so that socket 32 is firmly engaged with driving end 40. The surgeon grasps driver 12 by its handle (not shown) and positions screw 14A as illustrated in FIG. 5; i.e., screw 14A is received in the space between graft 50 and the interior wall of bore 48. Screw 14A is referred to herein as being received without interference into the space between the graft and the wall of the bore where asymmetrical side 24 is positioned flush against the graft 50. This describes the relative sizes of the screw and the gap between graft 50 and bore 48 and the fact that when screw 14A is positioned as shown in FIG. 5, no threads are engaged with either graft 50 or bore 48.

Figure 6:
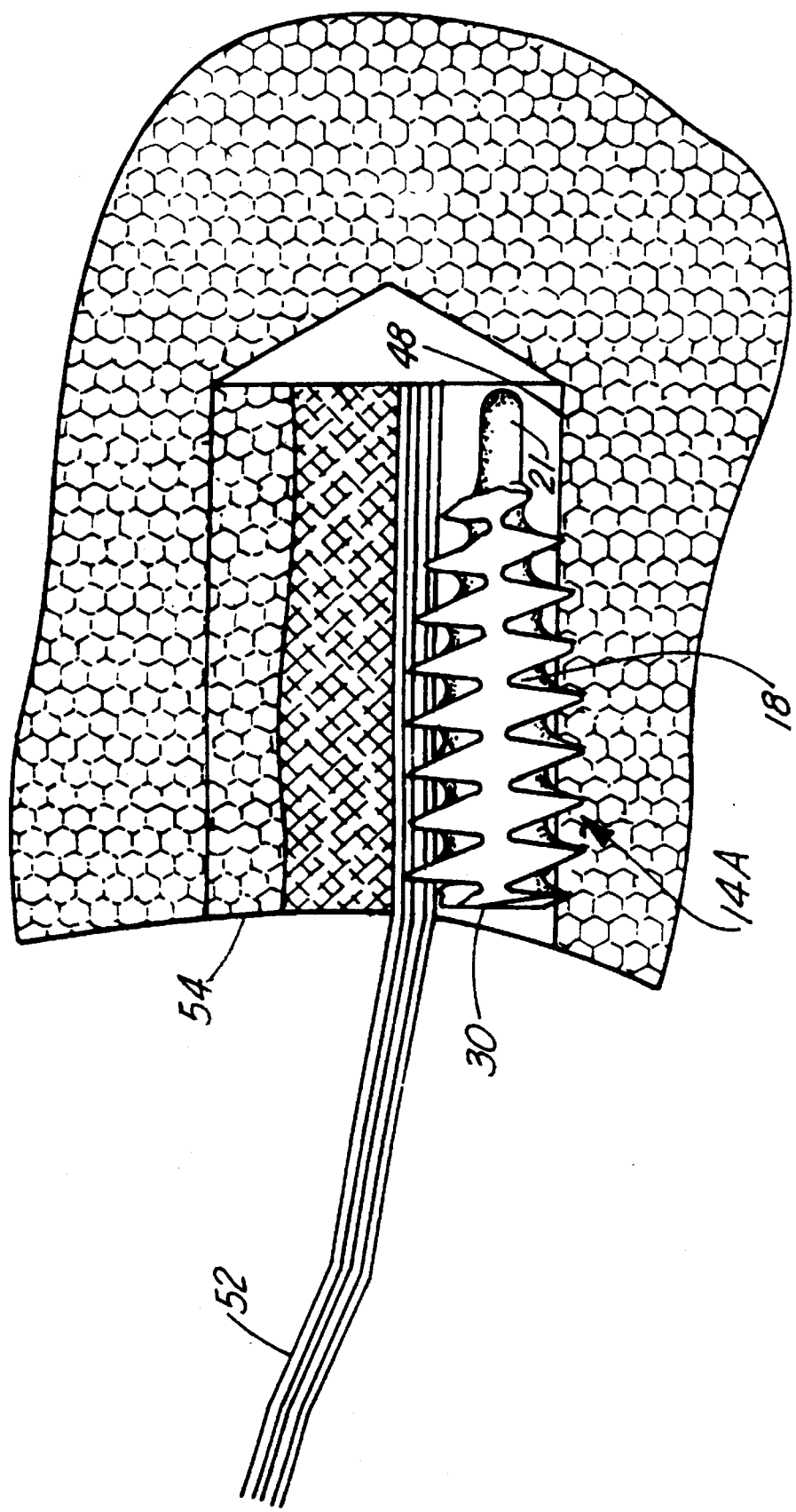
FIG. 6 is a view similar to FIG. 4, after the screw has been rotated and fully installed responsive to approximately 90° of screw rotation.

Next, the surgeon rotates screw 14A until the threads of the screw engage the graft 50 and bore 48, thereby locking the screw in place and fixing the graft in the bore, as shown in FIG. 6. Preferably, the surgeon rotates the screw approximately 90° to lock the screw into place. Once the screw is positioned as shown in FIG. 6, the surgeon may withdraw driving end 40 from socket 32. It should be noted that if it becomes necessary to remove the screw during a later surgical procedure, socket 32 cooperates with a standard hex driver. If a driver like driver 12 is not available when the screw is to be removed, it may be removed with a standard hex driver.

Other screws, like screw 14 or 14A, can be used in corresponding bores in the proximal tibia (not shown) to anchor the other end of graft 50 in a similar manner to that described above for anchoring the graft to the distal femur.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

I claim:

1. A method for securing a bone graft in an endosteal tunnel comprising:

drilling an endosteal bore of a size sufficient to form a space between the bone graft and a wall of the bore when the graft is inserted in the bore;

positioning the bone graft in the bore such that a space is formed between the graft and a wall of the bore;

selecting a biocompatible fixation device comprising a longitudinal body with a head at one end and thread crests extending circumferentially around only a portion of the body such that a portion of the body has a smooth face extending along the entire body;

slidingly inserting the selected device to such a depth into the space between the graft and the wall of the bore that the smooth face and thread crests contact bone and the head of the device is within the bore;

coupling a driving tool to the head of the fixation device; and rotating the screw through an angle such that threads of the device cut into and engage both the bone graft and the wall of the bore to form an interference fit that resists withdrawal of the graft from the bore.

2. The method according to claim 1 wherein the step of rotating the screw comprises no more than approximately 90°.

3. The method according to claim 1 including the step of fixing the graft in the bore wherein one side of the graft is flat along the longitudinal axis.

4. The method according to claim 1 wherein said device comprises an elongate nose with a rounded tip, said nose guiding the inserting of the device into the space between the bone graft and the wall of the bore.

5. The method according to claim 1 where said bore has an open end and a closed end.

6. A biocompatible cam-locking orthopedic fixation device for anchoring a bone graft in a bore formed in a bone mass, the device comprising:

a head comprising means for coupling a driving tool to the head, the head adapted for insertion into a space between a wall of a bore in bone and a bone graft in endosteal ligament reconstruction surgery;

a nose remote from the head;

a longitudinal body extending between the head and the nose of the device; the body having a uniform cross-section portion from the head of the device to about midway along the body and a tapered portion from about midway to the nose of the device and thread crests extending only partially circumferentially around the body along the uniform portion and the tapered portion, each thread crest extending to a height above the body.

7. The device of claim 6, wherein the nose is elongate in shape.

8. The device of claim 6, wherein the body has a substantially uniform pitch of about ten thread crests per inch.

\* \* \* \* \*